United States Patent
Ting et al.

(10) Patent No.: US 10,786,719 B2
(45) Date of Patent: Sep. 29, 2020

(54) SWIMMING POSTURE CORRECTION METHOD AND SWIMMING POSTURE CORRECTION SYSTEM

(71) Applicant: Industrial Technology Research Institute, Hsinchu (TW)

(72) Inventors: Tzu-Yang Ting, Taipei (TW); Yu-Hua Chung, Pingtung County (TW); Chieh-Wei Feng, Taoyuan (TW); Yen-Ting Wu, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 16/357,328

(22) Filed: Mar. 19, 2019

(65) Prior Publication Data

US 2020/0269113 A1 Aug. 27, 2020

(30) Foreign Application Priority Data

Feb. 25, 2019 (TW) ............................. 108106279 A

(51) Int. Cl.
*A63B 69/10* (2006.01)
*A63B 24/00* (2006.01)
(Continued)

(52) U.S. Cl.
CPC .......... *A63B 69/10* (2013.01); *A63B 24/0006* (2013.01); *A61B 5/1118* (2013.01);
(Continued)

(58) Field of Classification Search
CPC ................ A63B 69/10; A63B 24/0006; A63B 2024/0012; A63B 2220/10;
(Continued)

(56) References Cited

U.S. PATENT DOCUMENTS 7,980,998 B2 * 7/2011 Shemesh .............. A61B 5/1124
482/8
8,217,797 B2 * 7/2012 Ikoyan ................. A61B 5/4561
340/573.7
(Continued)

FOREIGN PATENT DOCUMENTS

| CN | 107115653 | * 11/2016 |
| CN | 108452504 | 8/2018 |
| TW | I632530 | 8/2018 |

*Primary Examiner* — Octavia Hollington
(74) *Attorney, Agent, or Firm* — JCIPRNET

(57) ABSTRACT

A swimming posture correction method and a swimming posture correction system, adapted for a computing apparatus to correct a swimming posture of a swimmer using at least two gravity sensors, are provided. The gravity sensors are respectively disposed at ends of at least two limbs of the swimmer performing a relative stroke action. In the method, body parameters of the swimmer are obtained and a reference index of coordination for implementing a swimming posture suitable for the body parameters is captured. A stroke of the limb is monitored using the gravity sensors to obtain a timing diagram of the limbs performing a stroke promotion action. Then, an index of coordination of the swimmer is calculated by analyzing the timing diagram and compared with the reference index of coordination so as to prompt for correcting the swimming posture according to a comparison result.

18 Claims, 12 Drawing Sheets

(51) Int. Cl.
*G16H 20/30* (2018.01)
*A61B 5/11* (2006.01)

(52) U.S. Cl.
CPC ... *A61B 2503/10* (2013.01); *A63B 2024/0012* (2013.01); *A63B 2220/10* (2013.01); *A63B 2220/30* (2013.01); *A63B 2244/20* (2013.01); *G16H 20/30* (2018.01)

(58) Field of Classification Search
CPC ............ A63B 2220/30; A63B 2244/20; A61B 5/1118; A61B 2503/10; G16H 20/30
USPC ...................................................... 73/379.01
See application file for complete search history.

(56) References Cited

U.S. PATENT DOCUMENTS

| | | |
|---|---|---|
| 10,060,745 B2 | 8/2018 | Ellis et al. |
| 2010/0210975 A1* | 8/2010 | Anthony, III ........ A61B 5/0002 600/595 |
| 2016/0038815 A1* | 2/2016 | Snell .................... A63B 69/125 4/492 |
| 2018/0117437 A1* | 5/2018 | Zhao ...................... A41D 1/002 |
| 2018/0249908 A1 | 9/2018 | Anthony et al. |

* cited by examiner

SWIMMING POSTURE CORRECTION METHOD AND SWIMMING POSTURE CORRECTION SYSTEM

CROSS-REFERENCE TO RELATED APPLICATION

This application claims the priority benefit of Taiwan application no. 108106279, filed on Feb. 25, 2019. The entirety of the above-mentioned patent application is hereby incorporated by reference herein.

TECHNICAL FIELD

The disclosure relates to an action monitoring method and a system, and also relates to a swimming posture correction method and a swimming posture correction system.

BACKGROUND

Nowadays, cycling, running and swimming are popularized as sport participation is increased. In general, users typically exercise in their own habits or comfortable postures, but athletes or ordinary exercisers may require correct movements in order to improve their performance. In addition to relying on coaching, they can also utilize electronic equipment as the aid to monitor their movement postures. For example, a swimmer can use a swimming training watch available on the market. The training watch detects the swimmer's swimming posture through a gravity sensor (G-sensor) and coordinates with a swimming efficiency algorithm, such as SWOLF (Swim-Golf), to calculate the swimming efficiency of the swimmer.

Although the swimmer can know the stroke efficiency from the swimming efficiency value, it is impossible to know the posture error when the efficiency is found to be poor, so the posture correction cannot be performed. Incorrect swimming posture is the key to the inability to improve swimming speed, so it is necessary to provide appropriate stroke feedback to the swimmer to assist with posture correction.

SUMMARY

The embodiments of the disclosure provide a swimming posture correction method. A computing device corrects a swimming posture of a swimmer by using at least two gravity sensors (G-sensors), and the G-sensors are respectively disposed at ends of at least two limbs of the swimmer performing a relative stroke action. The method includes obtaining body parameters of the swimmer to capture a reference index of coordination for implementing a swimming posture suitable for the body parameters, monitoring the stroke action of the limbs by using the G-sensors to obtain a timing diagram of the limbs performing a stroke promotion action, analyzing the timing diagram to calculate the index of coordination of the swimmer, and comparing the calculated index of coordination with the reference index of coordination to prompt for correcting the swimming posture according to the comparison result.

The embodiments in the disclosure provide a swimming posture correction system including at least two G-sensors and a computing device, wherein the G-sensors are respectively disposed at end of at least two limbs of the swimmer performing the relative stroke action. The computing device is communicatively connected to the G-sensors for obtaining the body parameters of the swimmer to capture a reference index of coordination for implementing a swimming posture suitable for the body parameters. The G-sensors are used to monitor the stroke action of the limbs to obtain a timing diagram of the limbs performing the stroke promotion action, and then the timing diagram is analyzed to calculate the swimmer's index of coordination. The calculated index of coordination is compared with the reference index of coordination to prompt for correcting the swimming posture according to the comparison result.

Several exemplary embodiments accompanied with figures are described in detail below to further describe the disclosure in details.

DESCRIPTION OF EMBODIMENTS

In the embodiment of the disclosure, a gravity sensor (G-sensor) is disposed on the swimmer to monitor the stroke action (including the speed, distance, efficiency, etc.) of the swimmer, along with combination of computing methods such as establishing a stroke timing diagram, calculating an index of coordination, comparing with database and so on, it is possible to instantly detect the posture problem of the swimmer, and to prompt the swimmer to correct the swimming posture through a wearing device (e.g., headset, swimming goggles). The embodiment of the disclosure further utilizes flow sensing, detection of body center axis and so on to correct the index value suitable for the water zone with respect to the flow rate of the water zone where the swimmer is located, and to prompt the swimmer to correct the swimming posture according to the deviation of the swimmer's body center axis.

Figure 1:
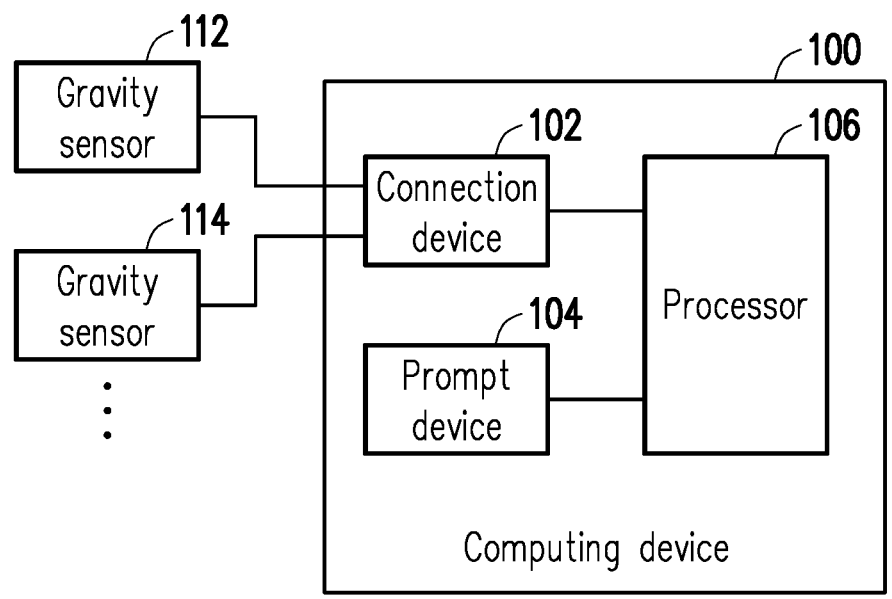
FIG. 1 is a block diagram of a swimming posture correction system according to an embodiment of the disclosure.

FIG. 1 is a block diagram of a swimming posture correction system according to an embodiment of the disclosure. Referring to FIG. 1, a swimming posture correction system 10 of the present embodiment includes a computing device 100 and at least two G-sensors (two G-sensors 112 and 114 are exemplified in the embodiment, but not limited thereto). In this embodiment, the G-sensors 112 and 114 are sensors independent of the computing device 100, and are connected to a connection device 102 of the computing device 100 to transmit the detected data to the computing device 100. This configuration allows the swimmer to dispose the G-sensors 112 and 114 flexibly with respect to the coordination of the limb portion to be monitored. For example, the G-sensors 112 and 114 may be disposed on the left and right wrists of the swimmer to monitor the coordination of both hands performing strokes, or the G-sensors 112 and 114 may be disposed on the left wrist and left ankle or right wrist and right ankle to monitor the coordination between the hand performing strokes and the leg performing kicks.

In other embodiments, one of the G-sensors 112 and 114 may also be directly disposed within the computing device 100 and integrated with the computing device 100 into a single device (e.g., integrated into a watch or bracelet). This configuration allows omission of additional computing device 100, thereby preventing hindering the swimmer's body movement. The embodiments of the disclosure are not limited to the above configuration.

The G-sensors 112 and 114, also known as accelerometers, acceleration sensors, etc., are devices for measuring acceleration, which can measure the acceleration of its own movement in the directions of three axes (X-axis, Y-axis, Z-axis). In other embodiments, the G-sensors 112 and 114 can also be used with a gyroscope to additionally measure the variation of roll, yaw and pitch. The above-described sensors or a combination thereof can assist in monitoring the swimming posture of the swimmer, and the embodiments of the disclosure provide no limitation to the types thereof.

The computing device 100 includes, for example, a connection device 102, a prompt device 104, and a processor 106. The connection device 102 is, for example, a device supporting a wireless connection method, and may be a wireless fidelity (Wi-Fi) module, a radio frequency identification (RFID) module, a Bluetooth module, an infrared ray module, a near-field communication (NFC) module or a device-to-device (D2D) module, but not limited thereto. In other embodiments, the connection device 102 may also be a device that supports a wired connection method, but not limited thereto.

The prompt device 104 is, for example, a speaker, and can be used to play a voice prompt message such as a voice message, a prompt tone, and an alert tone. The prompt device 104 can also be a display such as a liquid-crystal display (LCD) or a light-emitting diode (LED) display, which can be integrated into swimming goggles or a watch worn by the swimmer, thus prompting the swimmer to correct the swimming posture through visible prompt messages such as a display sign, a graphic or text. In the present embodiment, the prompt device 104 is disposed in the computing device 100. However, in other embodiments, the prompt device 104 may also be configured independently of the computing device 100 (e.g., configured in swimming goggles), and is connected with the connection device 102 of the computing device 100, thereby receiving the control instruction of the computing device 100 to play or display the prompt message accordingly.

The processor 106 is, for example, a central processing unit (CPU), or other programmable general-purpose or special-purpose microprocessor, a digital signal processor (DSP), a programmable controller, application specific integrated circuits (ASIC) or other similar devices or a combination of these devices. In this embodiment, the processor 106 can load a computer program from a storage device (not shown) such as a memory or a hard drive to perform the swimming posture correction method in the embodiment of the disclosure.

Figure 2:
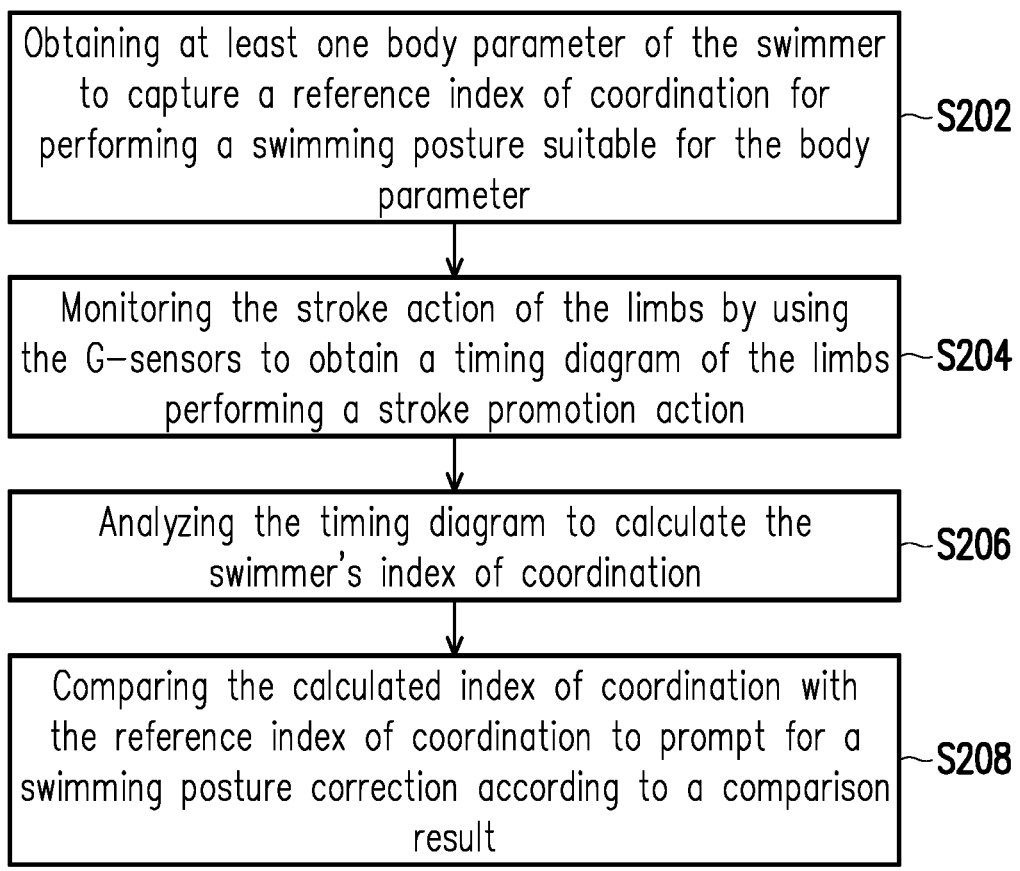
FIG. 2 is a flow chart of a swimming posture correction method according to an embodiment of the disclosure.

FIG. 2 is a flow chart of a swimming posture correction method according to an embodiment of the disclosure. Referring to FIG. 1 and FIG. 2, the method of the present embodiment is adaptable for the swimming posture correction system 10 of FIG. 1, and the swimming posture correction method in the disclosure is described in details below with reference to the actuation relationship between the devices in the swimming posture correction system 10.

In step S202, the computing device 100 obtains at least one body parameter (e.g., arm length, leg length, etc.) of the swimmer through the processor 106 to capture a reference index of coordination for implementing a swimming posture suitable for the body parameter. In an embodiment, the processor 106 can receive the body parameters input by the swimmer by using an input device such as a button, a touch pad, a touch screen, or the like disposed on the computing device 100. In other embodiments, the processor 106 can detect the body parameters (e.g., arm length, leg length, etc.) of the swimmer by using a sensor (e.g., G-sensors 112 and 114) disposed on the swimmer. Alternatively, the camera can be used to capture the body shape of the swimmer, and to identify the swimmer's body parameters by using an image identifying technology, or the body parameters of the swimmer can be obtained through any methods, the disclosure is not limited thereto. The above body parameters are, for example, height, weight, palm length, limb length or a combination thereof, but not limited thereto.

In addition, in an embodiment, the swimming posture correction system 100 further includes a remote server (not shown). The remote server is, for example, a cloud storage device or a cloud server which, for example, pre-measures the index of coordination under various conditions or a combination thereof with respect to different body shapes (e.g., height, weight), races, ages, swimming modes (e.g., competition, leisure, tutoring), swimming postures (e.g., freestyle, breaststroke, butterfly, backstroke) and so on to be used as reference index of coordination and centrally stored in the database of the remote server for the computing device 100 to make comparisons subsequently. In other embodiments, the database may also be established on the storage device of the computing device 100 itself, thus being accessed by the processor 106 at any time and applied to determining and prompting to correct swimming postures, the disclosure provides no limitation thereto.

In step S204, the processor 106 monitors the stroke action performed by the swimmer's limbs through the G-sensors 112 and 114, thereby obtaining a timing diagram of the limbs performing the stroke promotion action. In an embodiment, the processor 106 uses the G-sensors disposed on the swimmer's left and right wrists to monitor the stroke actions performed by both hands of the swimmer when the swimmer swims freestyle or backstroke. In an embodiment, the processor 106 uses the G-sensors disposed on the left wrist and left ankle or the right wrist and right ankle of the swimmer to monitor the stroke action performed by the left wrist and left ankle or the right wrist and right ankle of the swimmer when the swimmer swims butterfly or breaststroke.

Figure 3:
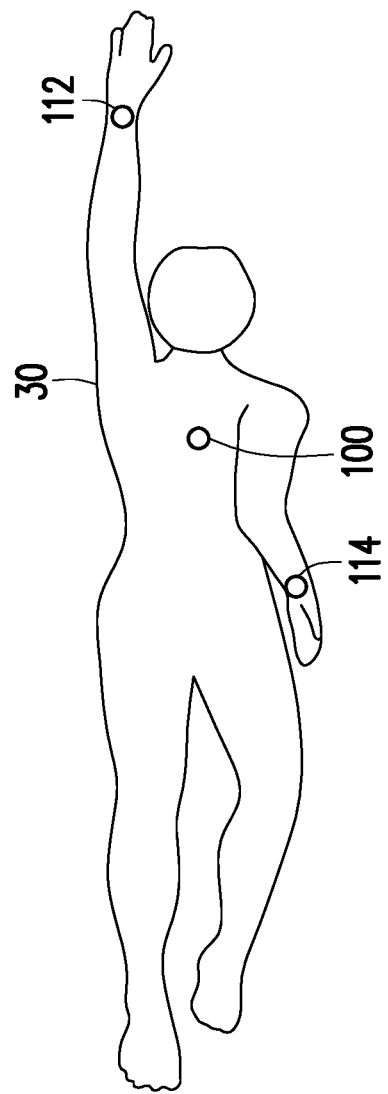
FIG. 3 is a configuration diagram of a swimming posture correction system according to an embodiment of the disclosure.

For example, FIG. 3 is a configuration diagram of a swimming posture correction system according to an embodiment of the disclosure. Referring to FIG. 1 and FIG. 3, the present embodiment shows that the G-sensors 112 and 114 of the swimming posture correction system 10 are respectively disposed on the left and right wrists of the swimmer 30, and the computing device 100 is disposed on the chest of the swimmer 30, such that the computing device 100 can monitor the stroke action performed by both hands of the swimmer 30 through the position variation of the left and right wrists detected by the G-sensor 112 and 114.

Figure 4:
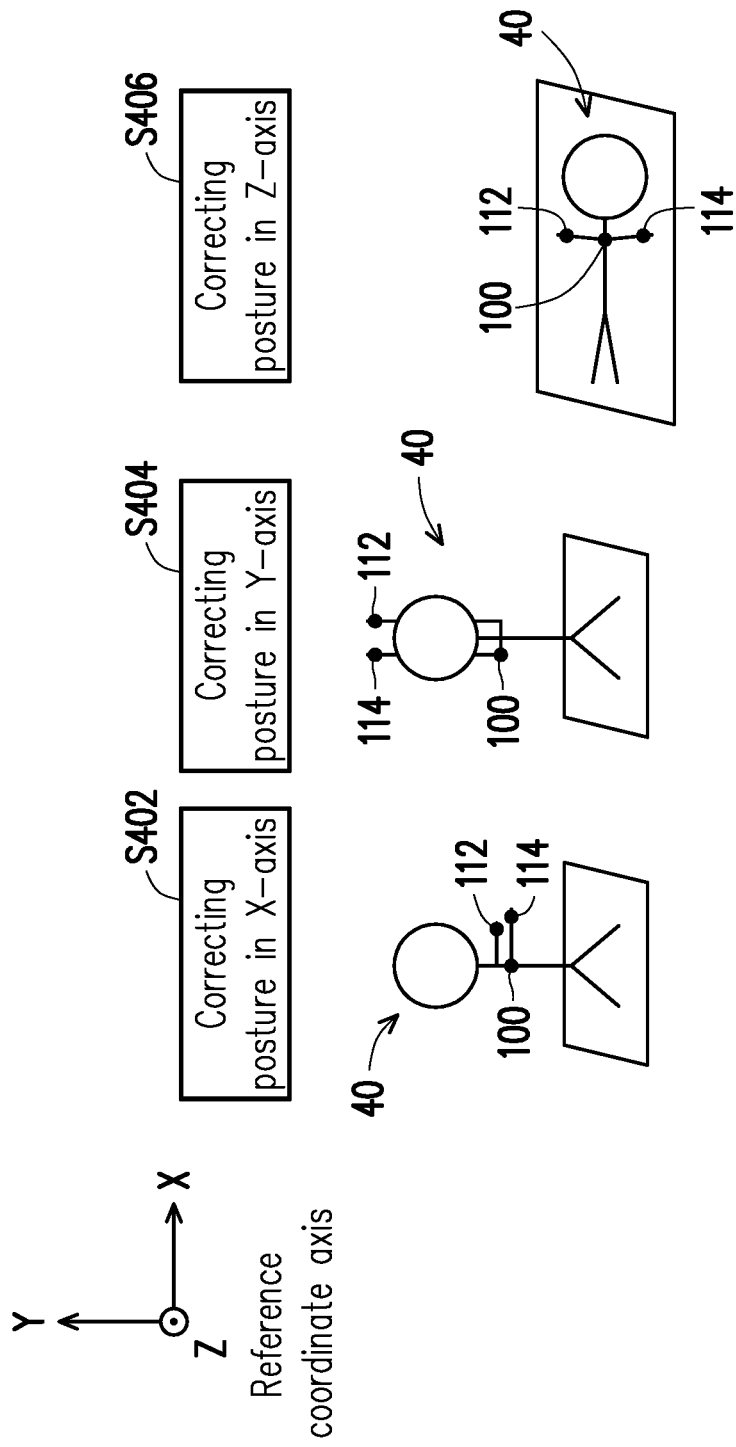
FIG. 4 is a schematic diagram illustrating performing correction by a gravity sensor according to an embodiment of the disclosure.

In an embodiment, the computing device 100, for example, corrects the position of the G-sensors 112 and 114 prior to monitoring the stroke action of the swimmer's limbs by using the G-sensors 112 and 114. For example, FIG. 4 is a schematic diagram illustrating performing correction by a G-sensor according to an embodiment of the disclosure. Referring to FIG. 1 and FIG. 4, in the present embodiment, for example, the computing device 100 is disposed on the shoulder of the swimmer 40, and G-sensors 112 and 114 are respectively disposed on the left wrist and the right wrist of the swimmer 40. The computing device 100, for example, is provided with a G-sensor (not shown).

In step S402, the processor 106 uses its own G-sensor as a reference point, prompting the swimmer 40 to lift his/her arm to the swimming forward direction (e.g., the X-axis direction in the figure) to perform an X-axis correction. In step S404, the processor 106 prompts the swimmer 40 to lift his/her arm to be right above (e.g., the Y-axis direction in the figure) the reference point to perform a Y-axis correction. In step S406, the processor 106 prompts the swimmer 40 to face the swimming forward direction, and his/her hands are opened to be parallel with the body (e.g., the Z-axis direction in the figure) to perform a Z-axis correction. It is assumed that during the above correction process, the position coordinates detected by the G-sensors of the computing device 100 are $(X_0, Y_0, Z_0)$, the position coordinates detected by the G-sensor 112 are $(X_1, Y_1, Z_1)$, the position coordinates detected by the G-sensor 114 are $(X_2, Y_2, Z_2)$, and the position coordinates of the computing device 100 after correction are (0, 0, 0), the position coordinates detected by the G-sensor 112 are $(X_1-X_0, Y_1-Y_0, Z_1-Z_0)$, and the position coordinates detected by the G-sensor 114 are $(X_2-X_0, Y_2-Y_0, Z_2-Z_0)$.

By the above correction process, the processor 106 can complete the position correction between the computing device 100 and the g-sensors 112 and 114, and even obtain the arm length of both hands of the swimmer 40. The processor 106 stores, for example, the correction result in the storage device of the computing device 100 itself as a basis for subsequent correction of the swimming posture.

In the present embodiment, the processor 106 detects the position of various limbs by using the G-sensors 112 and 114, and calculates the time at which the positions of various limbs are lower than the level surface (for instance, water surface) as the time of performing stroke promotion action. Then, the time and sequence of performing stroke promotion action by various limbs are used to establish the timing diagram of the stroke promotion action.

Figure 5A:
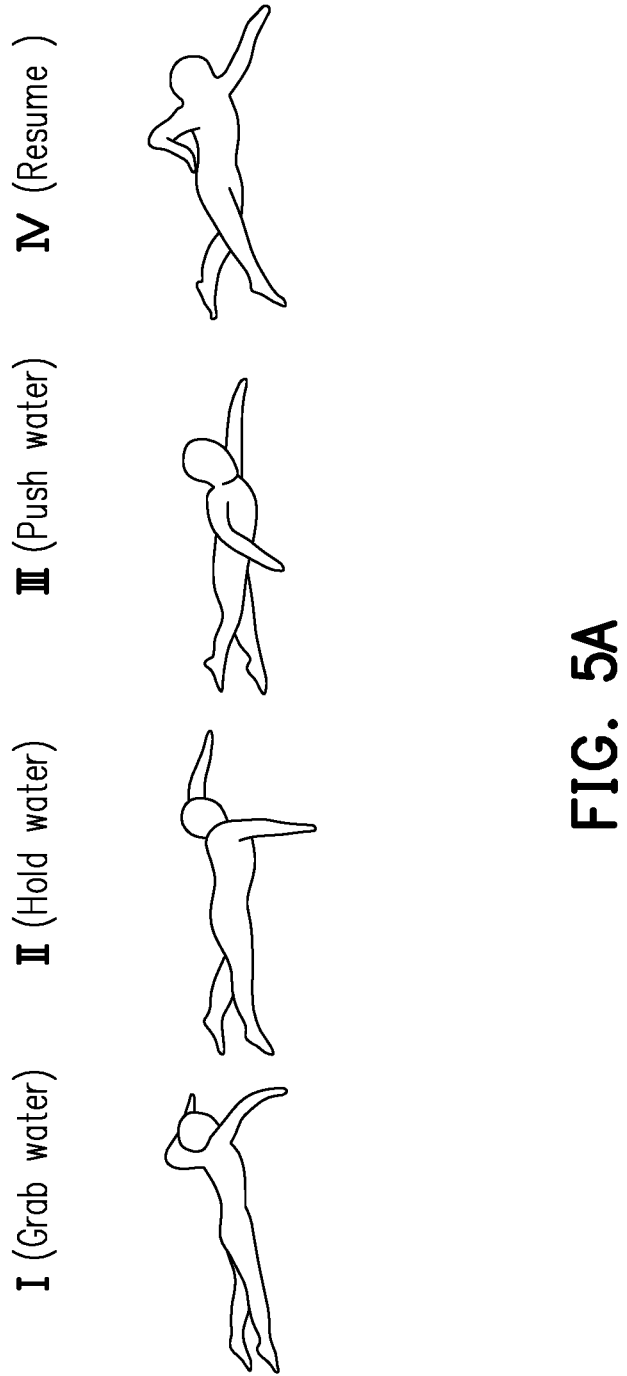
FIG. 5A is a schematic diagram illustrating a freestyle stroke action according to an embodiment of the disclosure.
Figure 5B:
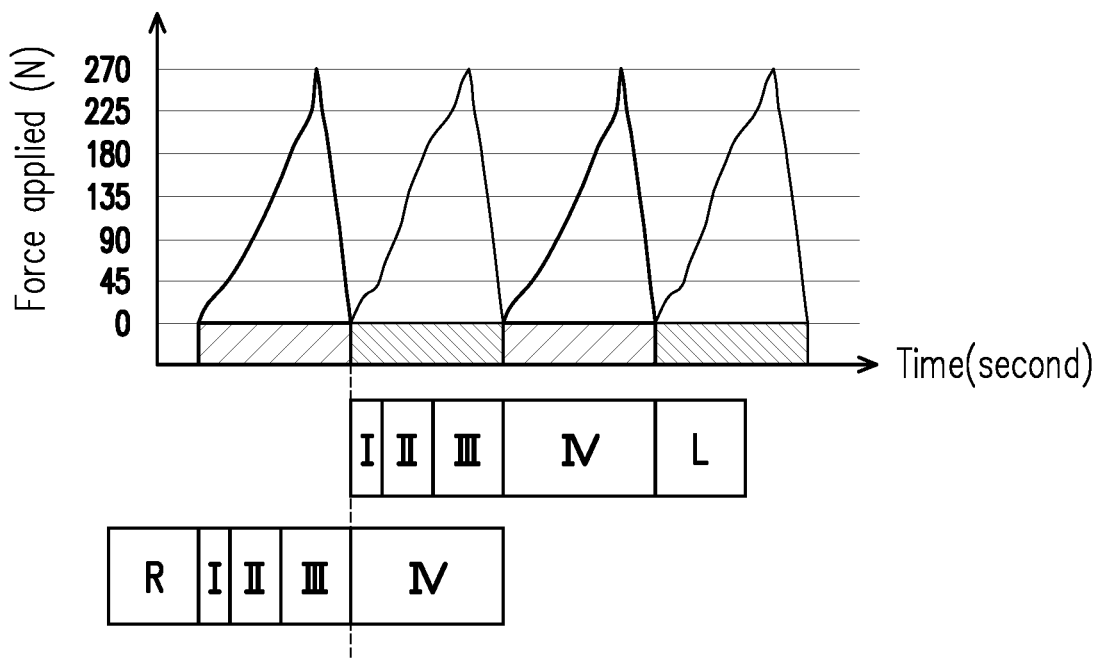
FIG. 5B to FIG. 5D are timing diagrams illustrating the stroke promotion action performed by a swimmer performing freestyle stroke action using both hands according to an embodiment of the disclosure.
Figure 5C:
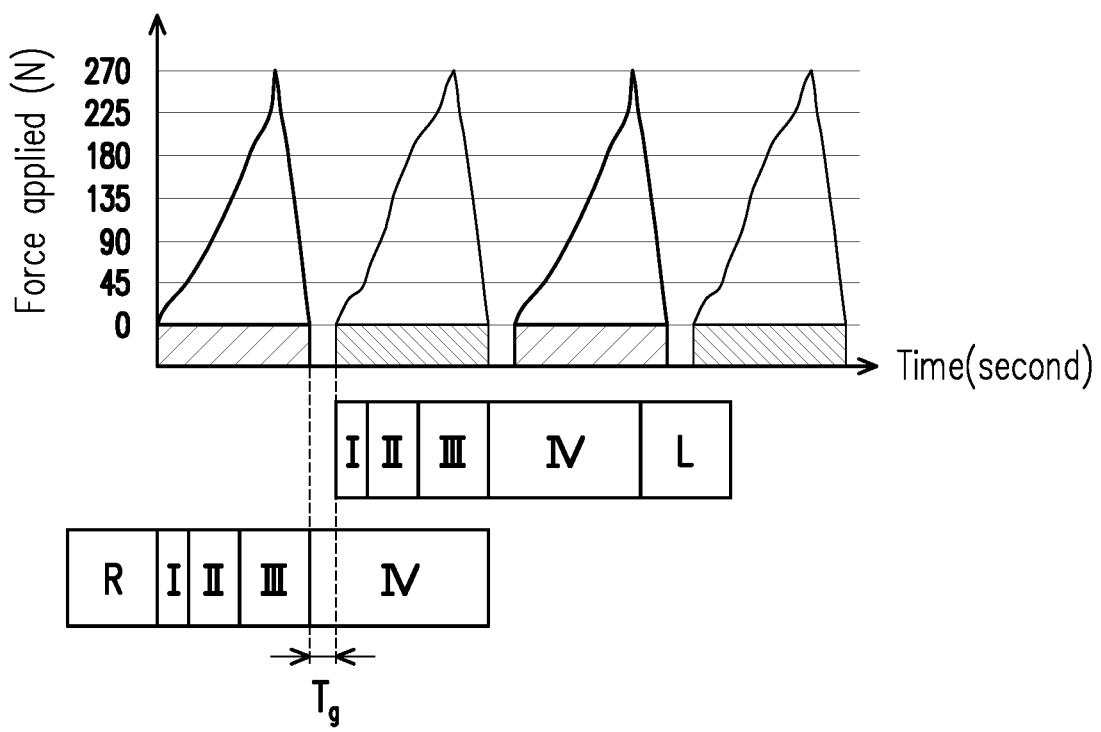
Figure 5D:
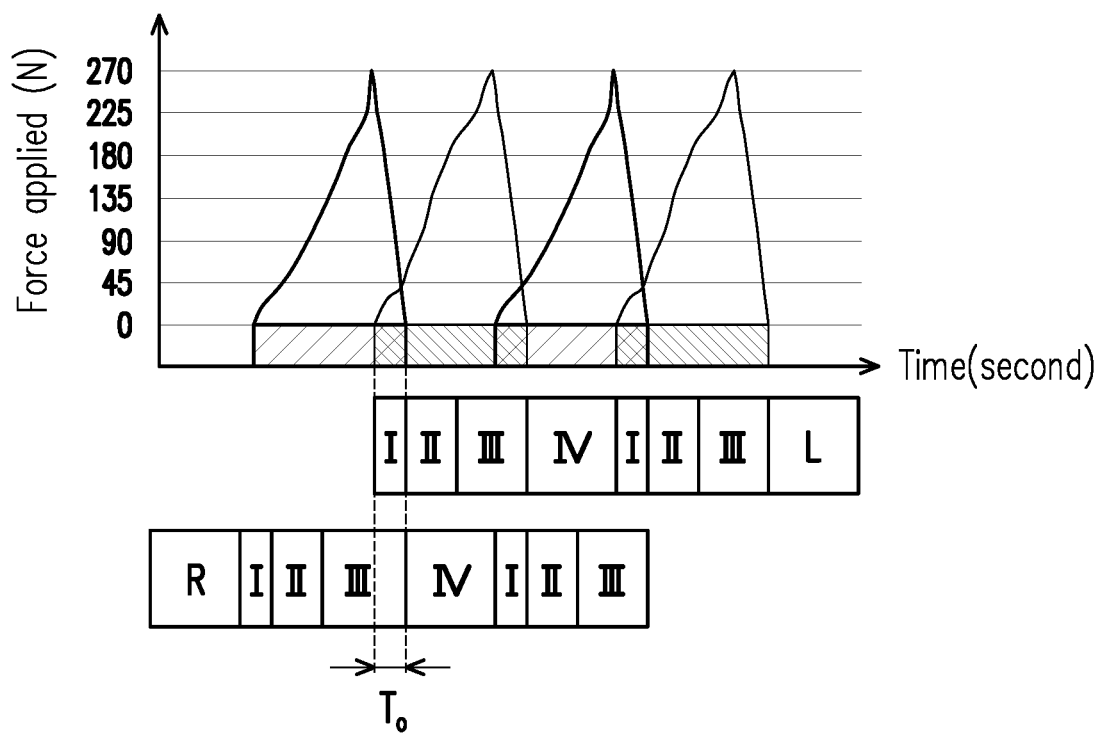

For example, FIG. 5A is a schematic diagram illustrating a freestyle stroke action according to an embodiment of the disclosure. Referring to FIG. 5A, this embodiment divides the swimmer's freestyle actions into four stages: stage I is grabbing water; stage II is holding water; stage III is pushing water; and stage IV is resuming. FIG. 5B to FIG. 5D are timing diagrams illustrating the stroke promotion action performed by a swimmer performing freestyle stroke action using both hands according to an embodiment of the disclosure. The timing diagram of FIG. 5B shows that, after the swimmer completes the water pushing action with right hand (stage III), left hand continues to perform the water grabbing action (stage I), which means that the swimmer performs the stroke promotion actions smoothly one after another with both hands and the stroke efficiency is better. The timing diagram of FIG. 5C shows that, after the swimmer completes the water pushing action (stage III) with his/her right hand and before performing the water grabbing action (stage I) with his/her left hand, there is an interval of time length $T_g$, which means that during the interval both of the swimmer's hands did not perform the stroke promotion action, thus affecting the stroke efficiency. The timing diagram of FIG. 5D shows that the swimmer's left hand performs the water grabbing action (stage I) before completing the water pushing action (stage III) with right hand, and there is an overlap of time length $T_o$, which means that both of the swimmer's hands perform the stroke promotion action during the overlap, indicating that force is applied repeatedly and stroke efficiency is affected accordingly.

This embodiment is directed to the timing diagram described above. In step S206, the processor 106 analyzes the timing diagram to calculate the swimmer's index of coordination. The processor 106, for example, calculates a time period in which each limb swings a complete circle, and calculates an interval time or an overlapping time (there is no interval time or overlapping time when the stroke promotion action of each limb is performed smoothly one after another) at which the limbs perform the stroke promotion actions respectively, thereby calculating the ratio of the interval time or overlapping time to the time period to be used as an index of coordination.

Figure 6:
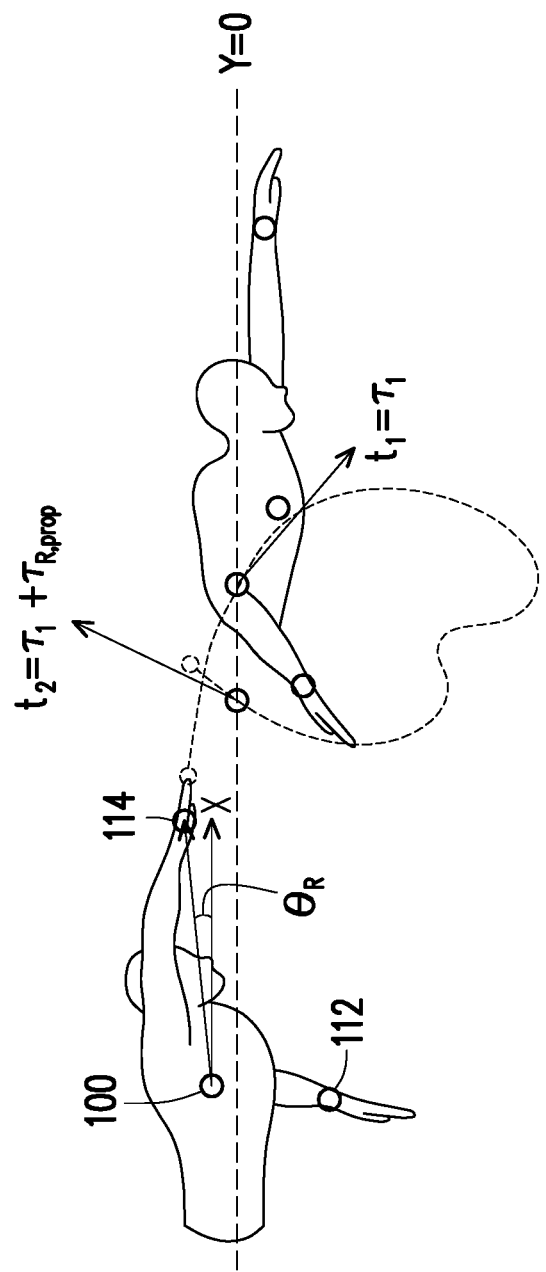
FIG. 6 is a schematic diagram illustrating calculating an index of coordination according to an embodiment of the disclosure.

For example, FIG. 6 is a schematic diagram illustrating calculating an index of coordination according to an embodiment of the disclosure. Referring to FIG. 6, in this embodiment, the computing device 100 receives the position coordinates returned by the G-sensors 112 and 114, and uses the position of the computing device 100 itself as the reference point to calculate the relative position coordinates of the G-sensors 112 and 114 relative to the computing device 100. The processor 106 of the computing device 100 can calculate the time period T in which the left hand and right hand swing a complete circle according to the variation of the relative position coordinates:

$$T=\Delta t|_{X\geq 0, \theta_R=0, Y=0} \quad (1)$$

Wherein X is the swimming forward direction, and $\theta_R$ is an included angle between the relative direction of the right wrist (i.e., G-sensor 114) relative to the computing device 100 and the X direction (i.e., the horizontal direction (Y=0)). At is the time required for the left wrist (or right wrist) to swing in a circle from the level surface ($\theta_R$=0, Y=0) ahead of the swimmer's head (X≥0) back to the level surface ahead of the swimmer's head in a clockwise direction or a counterclockwise direction (depending on the position of the observer).

On the other hand, the computing device 100 can calculate the time $\tau_{R,prop}$ for the right hand to perform the stroke promotion action:

$$\tau_{R,prop}=\Delta t|_{\Delta\theta_R=\pi, Y<0}=t_2-t_1 \quad (2)$$

As shown in the drawings, $\tau_{R,prop}$ represents the time at which the right wrist is below the level surface (Y=0), wherein $t_1$ represents the time at which the right wrist enters the water, $t_2$ represents the time at which the right wrist is lifted from the water. Similarly, the computing device 100 can calculate the time $\tau_{L,prop}$ at which the left hand performs the stroke promotion action.

Accordingly, the computing device 100 can calculate the reference index of coordination IdC through the following equation:

$$IdC=(\tau_{R,prop} \cap \tau_{L,prop})/T \quad (3)$$

Returning to the flowchart of FIG. 2, in step S208, the calculated index of coordination is compared with the reference index of coordination by the processor 106 to prompt for correcting the swimming posture according to the comparison result. The processor 106, for example, calculates an error between the index of coordination and the reference index of coordination, and determines whether the error is greater than a preset value (for example, 5% of the reference index of coordination), so as to prompt for correcting the swimming posture when the error is greater than the preset value. In an embodiment, the processor 106, for example, sends a control instruction to the prompt device 104, thereby controlling the prompt device 104 to play or display a prompt message to prompt the user to correct the swimming posture. The prompt message includes a voice message, a prompt tone, an alert tone, a sign, a graphic or text, and the content thereof is, for example, prompting the user to speed up/slow down the stroke action performed by the left hand/right hand, but not limited thereto.

By the above method, the swimming posture correction system 10 in the embodiment of the disclosure can determine the error between the stroke action of the swimmer and the stroke action performed by the same group of swimmers by monitoring the stroke action performed by the swimmer, thereby instantly and properly prompting the swimmer to correct the swimming posture.

On the other hand, for the flow rate of the water zone in which the swimmer swims, an embodiment of the disclosure further includes providing a pressure sensor (not shown) on the portion (for example, the head or the shoulder) of the swimmer which does not perform the swimming action to detect the water resistance encountered by the swimmer, thereby updating the calculated index of coordination.

Figure 7:
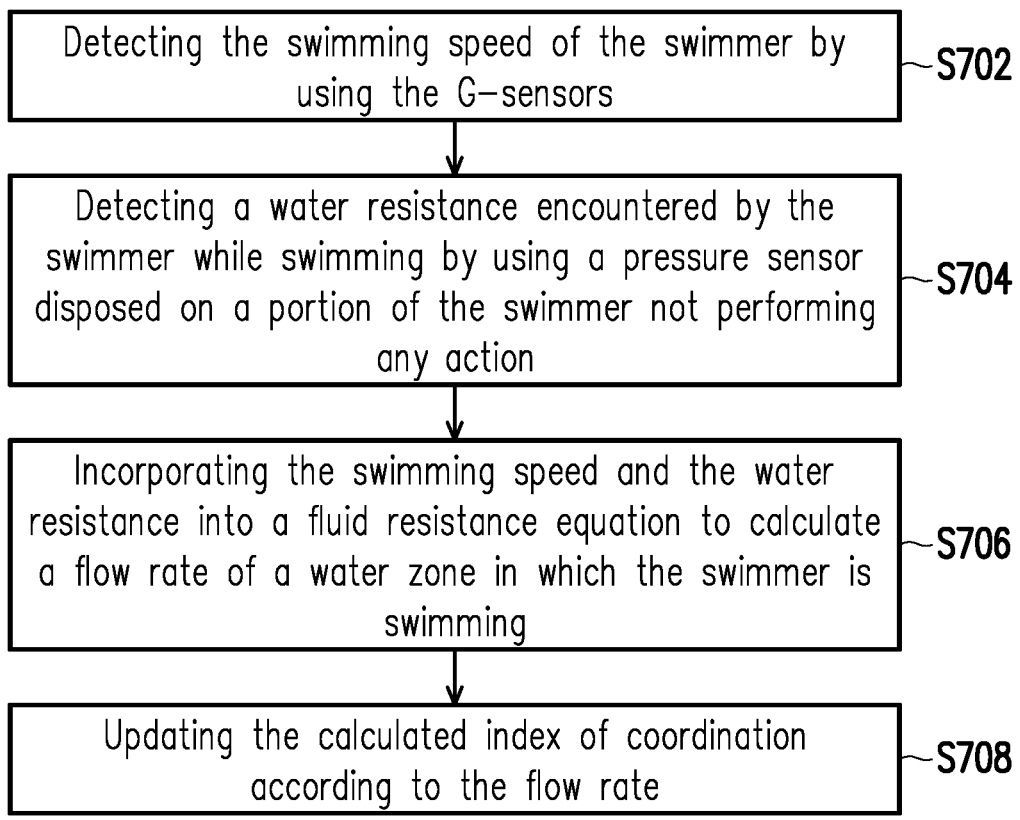
FIG. 7 is a flow chart of a swimming posture correction method according to an embodiment of the disclosure.

FIG. 7 is a flow chart of a swimming posture correction method according to an embodiment of the disclosure. Referring to FIG. 1 and FIG. 7, the method of the present embodiment is, for example, performed subsequently after step S206 of FIG. 2, thereby appropriately updating the index of coordination calculated in step S206 according to the flow rate of the water flow.

In step S702, the computing device 100 detects the swimming speed of the swimmer by the processor 106 using the G-sensors 112 and 114. The processor 106 can calculate the swimming speed v of the swimmer according to the variation of the position coordinates detected by the G-sensors 112 and 114 (wherein $\Delta x$ is the moving distance of the swimmer, and t is the time spent on moving):

$$v = \Delta x/t \quad (4)$$

In step S704, the processor 106 uses the pressure sensor to detect the water resistance encountered by the swimmer. The processor 106 calculates the water resistance $f_d$ according to the pressure value P detected by the pressure sensor and the cross-sectional area A of the pressure sensor:

$$f_d = P \times A \quad (5)$$

In step S706, the processor 106 incorporates the swimming speed v and the water resistance $f_d$ calculated in the foregoing steps into the following fluid resistance equation (6), thereby calculating the flow rate $\omega$ of the water zone in which the swimmer swims:

$$F = \frac{1}{2}\rho(v+\omega)^2 C_d A \quad (6)$$

Wherein F is the water resistance $f_d$, $\rho$ is the density of the fluid, and $C_d$ is a constant.

Figure 8A:
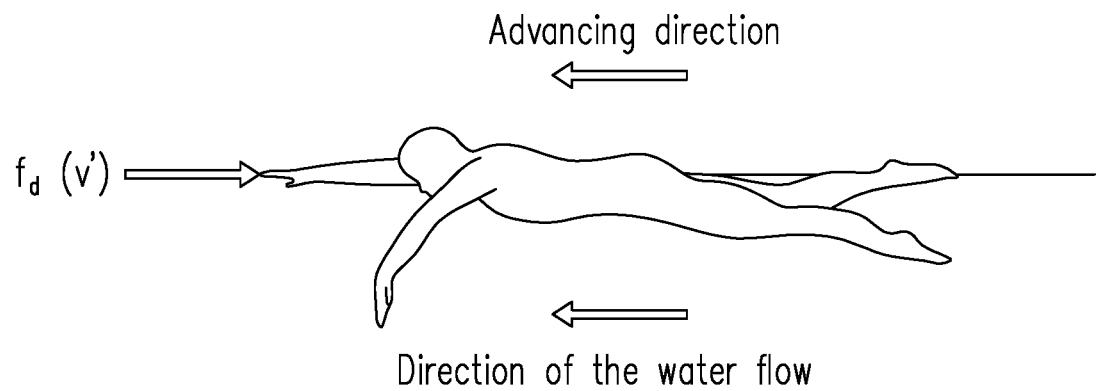
FIG. 8A and FIG. 8B are schematic diagrams illustrating correction of water flow according to an embodiment of the disclosure.
Figure 8B:
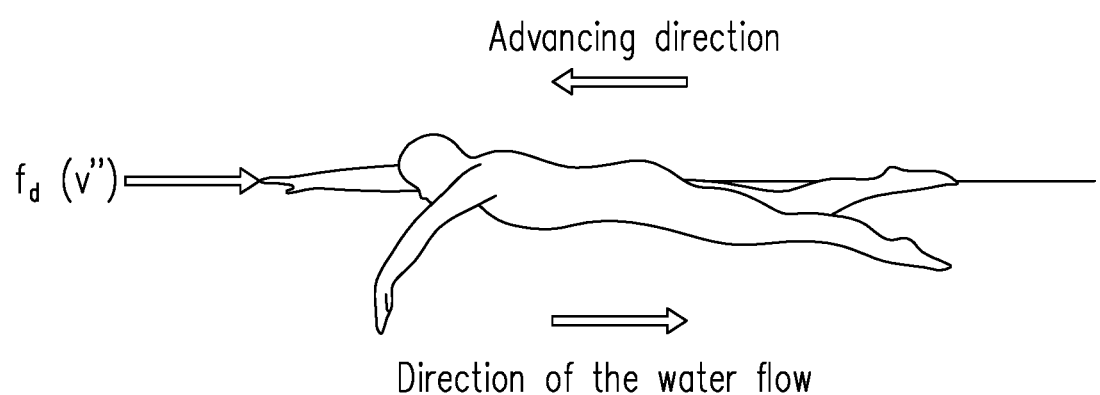

For example, FIG. 8A and FIG. 8B are schematic diagrams illustrating correction of water flow according to an embodiment of the disclosure. Referring to FIG. 8A, in the case of a forward flow (i.e., the swimmer's advancing direction is the same as the direction of the water flow), the swimmer will be subjected to a water resistance $f_d(v')$ of which the speed is v', wherein the speed v'=v−$\omega$). The swimming speed v detected by the G-sensor and the water resistance $f_d(v')$ detected by the pressure sensor are incorporated into the fluid resistance equation (6) to calculate the flow rate $\omega$:

$$\frac{2f_d(v')}{\rho C_d A} = (v')^2 = (v-\omega)^2 \quad (7)$$

Referring to FIG. 8B, in the case of a backward flow (i.e., the swimmer's advancing direction is opposite to the direction of the water flow), the swimmer will be subjected to a water resistance $f_d(v'')$ of which the speed is v'', wherein the speed v''=v+$\omega$. The swimming speed v detected by the G-sensor and the water resistance $f_d(v'')$ detected by the pressure sensor are incorporated into the fluid resistance equation (6) to calculate the flow rate $\omega$:

$$\frac{2f_d(v'')}{\rho C_d A} = (v'')^2 = (v+\omega)^2 \quad (8)$$

Returning to the flow chart of FIG. 7, in step S708, the processor 106 updates the previously calculated index of coordination according to the calculated flow rate. Specifically, in the case of forward flow, the processor 106, for example, reduces the index of coordination; in the case of backward flow, the processor 106 increases the index of coordination.

In addition, for the swimming posture of the swimmer, an embodiment of the disclosure further includes providing a G-sensor on the swimmer's hands and feet to detect the horizontal axis of the body when the swimmer swims, thereby determining whether the swimming posture is correct according to the degree (angle) at which the body horizontal axis is deviated from the level surface to prompt for correction.

Figure 9:
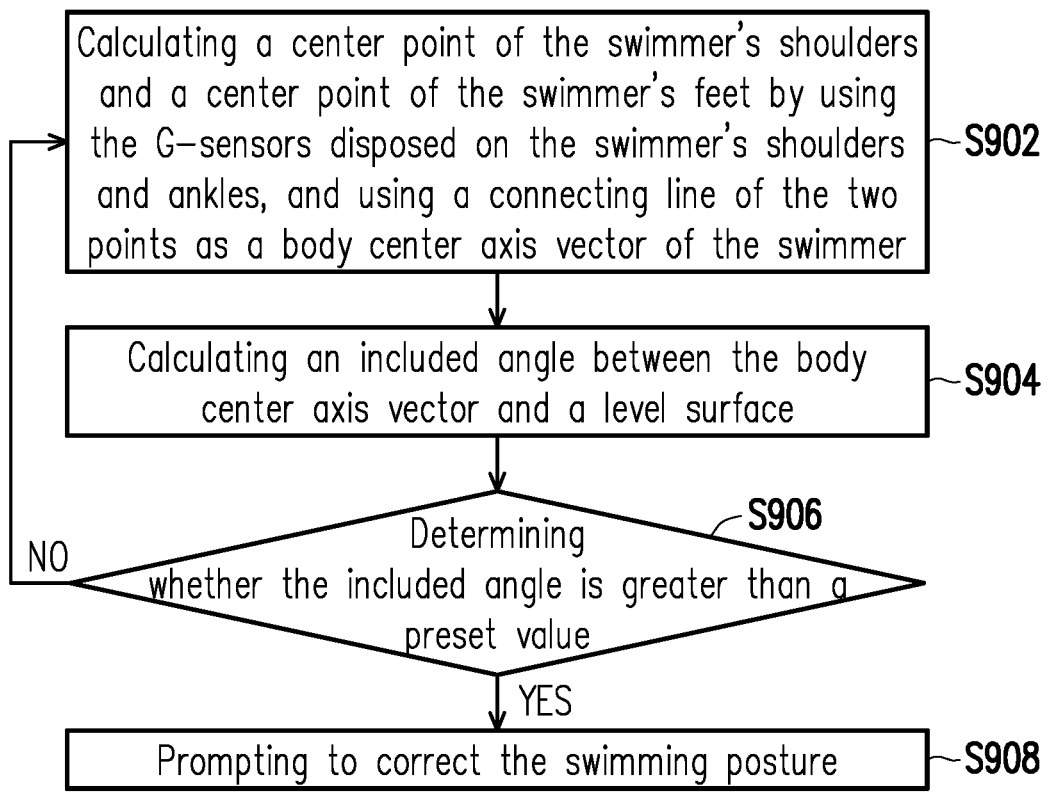
FIG. 9 is a flow chart of a swimming posture correction method according to an embodiment of the disclosure.

FIG. 9 is a flow chart of a swimming posture correction method according to an embodiment of the disclosure. Referring to FIG. 1 and FIG. 9, in an embodiment, the method of the embodiment is applied, for example, in step S208 of FIG. 2, before the processor 106 of the computing device 100 prompts the swimmer to correct the swimming posture by using the prompt device 114, the degree at which the swimmer's body horizontal axis is deviated from the level surface is determined first, thereby prompting the swimmer to perform a corresponding posture correction. In other embodiments, the method of the present embodiment can be applied to any step in FIG. 2 to prompt the swimmer to correct the swimming posture at any time, the disclosure provides no limitation thereto.

In step S902, the computing device 100 calculates the center point between shoulders and the center point between two feet by the processor 106 through the G-sensors disposed on the swimmer's shoulders and ankles, and uses the connecting line between the two points as the swimmer's body center axis vector. In an embodiment, the computing device 100 is disposed, for example, at a position of the swimmer's chest near the center point of the shoulders, such that the processor 106 can calculate the position coordinate of the center point of the shoulders through the G-sensor (not shown) disposed in the computing device 100. In addition, the G-sensor is disposed, for example, on the left ankle or right ankle of the swimmer, such that the processor 106 can use the G-sensor to calculate the position coordinate of the center point of the two feet. Accordingly, the processor 106 can calculate the body center axis vector of the swimmer.

In step S904, the included angle between the body center axis vector and the level surface is calculated by the processor 106, and in step S906, it is determined whether the calculated included angle is greater than a preset value. The preset value is, for example, any value between −30 degrees and 30 degrees, and the disclosure provides no limitation thereto. The included angle is a positive value (ideal value is, for example, less than 20 degrees) when the swimmer breathes, and is a negative value when the swimmer dives into the water. Generally, a larger included angle (−10 degrees to 20 degrees) is generated when the swimmer breathes. When the included angle is close to 0 degree, the resistance encountered by the swimmer will be reduced and the swimming speed of swimming will increase. Accordingly, the swimmer can adjust the preset value as needed to use the prompt of the computing device 100 to assist him/her in improving the swimming speed.

In step S908, when the processor 106 determines that the calculated included angle is greater than the preset value, it is determined that the inclination of the swimmer's body at this time will cause the stroke route to increase, and the resistance becomes larger, resulting in decrease of index of coordination. As a result, the prompt device 104 is controlled by prompt the user to correct the swimming posture. For example, the swimmer may be prompted to speed up the kicking speed or reduce the lifting force of the hands to stroke, so that the body can resume to the horizontal standard.

Figure 10:
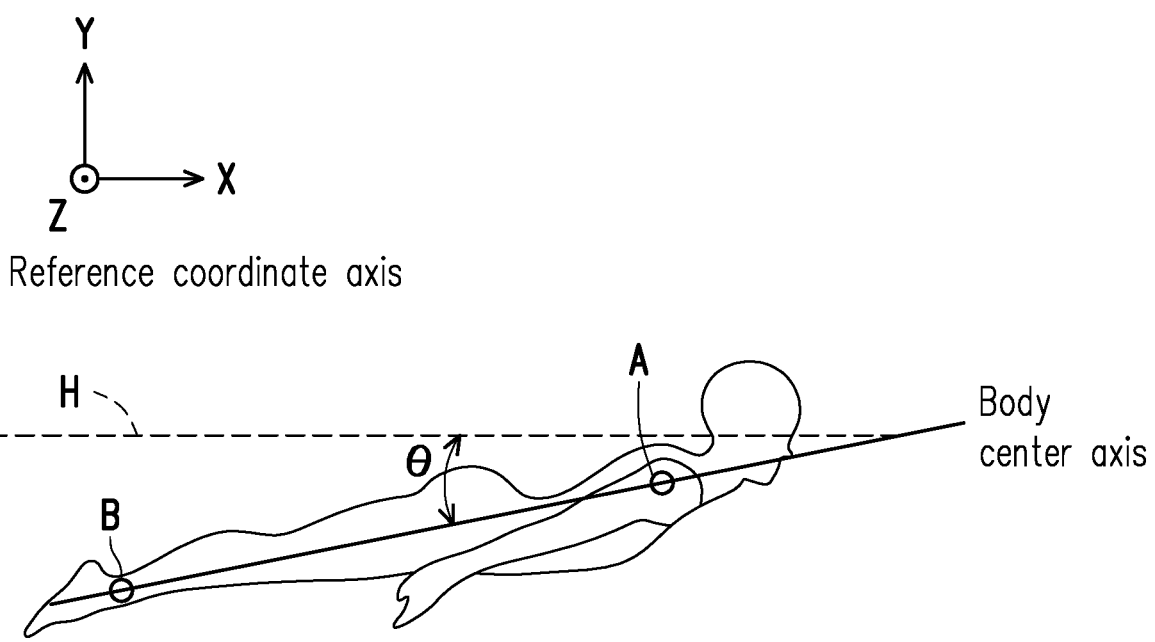
FIG. 10 is a schematic diagram illustrating a body center axis of a swimmer according to an embodiment of the disclosure.

For example, FIG. 10 is a schematic diagram illustrating a body center axis of a swimmer according to an embodiment of the disclosure. Referring to FIG. 10, in this embodiment, a G-sensor A is disposed on the shoulder of the swimmer, and a G-sensor B is disposed on the swimmer's ankle, such that the vector of the body center axis as well as an included angle θ between the body center axis vector and the horizontal vector H (for instance, level surface) can be calculated according to the position coordinates detected by the G-sensor A and the G-sensor B. By determining whether the calculated included angle θ exceeds the preset value (e.g., 15 degrees), and when it is determined that the included angle θ exceeds the preset value, the swimmer is prompted to correct the swimming posture. In this manner, it is possible to remind the swimmer to correct the posture instantly during the swimming process, thereby improving the swimming efficiency.

In summary, the swimming posture correction method and system of the embodiments of the disclosure monitor the coordination of the stroke action by configuring the G-sensor on the limbs of the swimmer performing stroke actions, by comparing with the data of the same group in the database, it is possible to instantly detect the posture problem of the swimmer and prompt the swimmer to correct the swimming posture. The method in the disclosure further combines the techniques of flow rate sensing and body center axis detection to assist the swimmer in properly performing posture correction with respect to the flow rate of the water zone where the swimmer is located and body inclination of the swimmer, thereby improving swimming efficiency.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A swimming posture correction method adapted to correct a swimming posture of a swimmer by a computing device using at least two gravity sensors (G-sensors), wherein the G-sensors are respectively disposed at ends of at least two limbs of the swimmer performing a relative stroke action, the method comprising the steps of:
   obtaining at least one body parameter of the swimmer to capture a reference index of coordination for performing a swimming posture suitable for the body parameter;
   monitoring the stroke action of the at least two limbs by using the G-sensors to obtain a timing diagram of the at least two limbs performing a stroke promotion action;
   analyzing the timing diagram to calculate an index of coordination of the swimmer; and
   comparing the calculated index of coordination with the reference index of coordination to prompt for correcting the swimming posture according to a comparison result,
   wherein the step of obtaining the timing diagram of the at least two limbs performing the stroke promotion action by monitoring the stroke action of the at least two limbs through using the G-sensors comprises:
   detecting a position of each of the limbs by using the G-sensors;
   calculating a time at which the position of each of the limbs is below level surface as a time of performing the stroke promotion action; and
   establishing the timing diagram of the stroke promotion action by using the calculated time and a sequence of performing the stroke promotion action by each of the limbs.

2. The swimming posture correction method of claim 1, wherein the step of analyzing the timing diagram to calculate the index of coordination of the swimmer comprises:
   calculating a time period during which each of the limbs swings a complete circle; and
   calculating an interval time or an overlapping time at which the stroke promotion action is performed by the at least two limbs respectively, and calculating a ratio of the interval time or the overlapping time to the time period as the index of coordination.

3. The swimming posture correction method of claim 1, wherein the step of comparing the calculated index of coordination with the reference index of coordination to prompt for correcting the swimming posture according the comparison result comprises:
   calculating an error between the index of coordination and the reference index of coordination, and determining whether the error is greater than a preset value; and
   if the error is greater than the preset value, prompting for correcting the swimming posture.

4. The swimming posture correction method of claim 1, wherein before the step of using the G-sensors to monitor the stroke action of the at least two limbs, the method further comprising:

using a G-sensor disposed at a shoulder position of the swimmer as a reference point, prompting the swimmer to lift an arm to a swimming forward direction for an X-axis correction, prompting the swimmer to lift the arm to be right above the reference point for a Y-axis correction; and prompting the swimmer to face the swimming forward direction with both hands opened to be parallel to the body for a Z-axis correction.

5. The swimming posture correction method of claim 1, wherein after the step of analyzing the timing diagram to calculate the index of coordination of the swimmer, the method further comprising:

using the G-sensors to detect a swimming speed of the swimmer;

detecting a water resistance encountered by the swimmer while swimming by using a pressure sensor disposed on a portion of the swimmer not performing any action;

incorporating the swimming speed and the water resistance into a fluid resistance equation to calculate a flow rate of a water zone in which the swimmer is swimming; and updating the calculated index of coordination according to the flow rate.

6. The swimming posture correction method of claim 1, wherein the step of monitoring the stroke action of the at least two limbs by using the G-sensors comprises:

monitoring the stroke action performed by a left hand and a right hand of the swimmer when the swimmer swims freestyle or backstroke by using the G-sensors disposed on a left wrist and a right wrist of the swimmer.

7. The swimming posture correction method of claim 1, wherein the step of monitoring the stroke action of the at least two limbs by using the G-sensors comprises:

monitoring the stroke action of a left wrist and a left ankle or a right wrist and a right ankle of the swimmer when the swimmer swims butterfly or breaststroke by using the G-sensors disposed on the left wrist and the left ankle or the right wrist and the right ankle of the swimmer.

8. The swimming posture correction method of claim 1, further comprising:

calculating a center point of shoulders and a center point of feet of the swimmer by using the G-sensors disposed on the shoulders and ankles of the swimmer, and using a connecting line between the two points as a body center axis vector of the swimmer;

calculating an included angle between the body center axis vector and horizontal vector, and determining whether the included angle is greater than a preset value; and if the included angle is greater than the preset value, prompting for correcting the swimming posture.

9. The swimming posture correcting method of claim 1, wherein the body parameter comprises at least one of height, weight, palm length, and limb length.

10. A swimming posture correction system, comprising:

at least two G-sensors, respectively disposed at ends of at least two limbs of a swimmer performing a relative stroke action; and a computing device, communicatively connected to the G-sensors, configured for:

obtaining at least one body parameter of the swimmer to capture a reference index of coordination for performing a swimming posture suitable for the body parameter;

monitoring the stroke action of the at least two limbs by using the G-sensor to obtain a timing diagram of the at least two limbs performing a stroke promotion action;

analyzing the timing diagram to calculate an index of coordination of the swimmer; and comparing the calculated index of coordination with the reference index of coordination to prompt for correcting the swimming posture according to a comparison result, wherein the computing device further configured for:

detecting a position of each of the limbs by using the G-sensors;

calculating a time at which the position of each of the limbs is below level surface as a time of performing the stroke promotion action; and establishing the timing diagram of the stroke promotion action by using the calculated time and a sequence of performing the stroke promotion action by each of the limbs.

11. The swimming posture correction system of claim 10, wherein the computing device comprises:

calculating a time period during which each of the limbs swings a complete circle; and calculating an interval time or an overlapping time at which the stroke promotion action is performed by the at least two limbs respectively, and calculating a ratio of the interval time or the overlapping time to the time period as the index of coordination.

12. The swimming posture correction system of claim 10, wherein the computing device comprises:

calculating an error between the index of coordination and the reference index of coordination, and determining whether the error is greater than a preset value; and if the error is greater than the preset value, prompting for correcting the swimming posture.

13. The swimming posture correction system of claim 10, wherein the computing device further comprises:

using a G-sensor disposed at a shoulder position of the swimmer as a reference point, prompting the swimmer to lift an arm to a swimming forward direction for an X-axis correction, prompting the swimmer to lift the arm to be right above the reference point for a Y-axis correction; and prompting the swimmer to face the swimming forward direction with both hands opened to be parallel to the body for a Z-axis correction.

14. The swimming posture correction system of claim 10, wherein the computing device further comprises:

using the G-sensors to detect a swimming speed of the swimmer;

detecting a water resistance encountered by the swimmer while swimming by using a pressure sensor disposed on portion of the swimmer not performing any action;

incorporating the swimming speed and the water resistance into a fluid resistance equation to calculate a flow rate of a water zone in which the swimmer is swimming; and updating the calculated index of coordination according to the flow rate.

15. The swimming posture correction system of claim 10, wherein the G-sensors are disposed on a left wrist and a right wrist of the swimmer for monitoring the stroke action performed by a left hand and a right hand of the swimmer when the swimmer swims freestyle or backstroke.

16. The swimming posture correction system of claim 10, wherein the G-sensors are disposed on a left wrist and a left ankle or a right wrist and a right ankle of the swimmer for monitoring the stroke action of the left wrist and the left ankle or the right wrist and the right ankle of the swimmer when the swimmer swims butterfly or breaststroke.

17. The swimming posture correction system of claim 10, wherein the G-sensors are disposed on shoulders and ankles of the swimmer, and the computing device comprises:
   calculating a center point of the shoulders and a center point of feet of the swimmer by using the G-sensors, and using a connecting line between the two points as a body center axis vector of the swimmer;
   calculating an included angle between the body center axis vector and horizontal vector, and determining whether the included angle is greater than a preset value; and
   if the included angle is greater than the preset value, prompting for correcting the swimming posture.

18. The swimming posture correction system of claim 10, wherein one of the G-sensors is disposed in the computing device.

* * * * *